United States Patent
Bonjour

[19]
[11] Patent Number: 5,904,674
[45] Date of Patent: May 18, 1999

[54] DISPOSABLE ABSORBENT SANITARY ARTICLE WITH STRETCHABLE LONGITUDINAL SEALS FORMING A POUCH

[75] Inventor: Emmanuel Bonjour, Messery, France

[73] Assignee: SCA Molnlycke, Linselles, France

[21] Appl. No.: 08/860,872

[22] PCT Filed: Jan. 17, 1996

[86] PCT No.: PCT/FR96/00071

§ 371 Date: Aug. 5, 1997

§ 102(e) Date: Aug. 5, 1997

[87] PCT Pub. No.: WO96/22755

PCT Pub. Date: Aug. 1, 1996

[30] Foreign Application Priority Data

Jan. 23, 1995 [FR] France .................................. 95 00918

[51] Int. Cl.⁶ .................................................. A61F 13/15
[52] U.S. Cl. ...................................... 604/385.2; 604/385.1
[58] Field of Search ............................. 604/385.1, 385.2, 604/393, 394, 395, 396, 397, 398

[56] References Cited

U.S. PATENT DOCUMENTS

| | | | |
|---|---|---|---|
| 4,662,877 | 5/1987 | Williams . | |
| 5,021,051 | 6/1991 | Hiuke | 604/385.2 |
| 5,304,159 | 4/1994 | Tanji et al. | 604/385.2 |
| 5,304,160 | 4/1994 | Igaue et al. . | |
| 5,342,342 | 8/1994 | Kitaoka . | |
| 5,429,632 | 7/1995 | Tanji et al. . | |
| 5,575,785 | 11/1996 | Gryskiewicz et al. | 604/385.2 |

FOREIGN PATENT DOCUMENTS

| | | | |
|---|---|---|---|
| 357 298 | 3/1990 | European Pat. Off. . | |
| 508 477 | 10/1992 | European Pat. Off. . | |
| 563 971 | 10/1993 | European Pat. Off. . | |
| 565 058 | 10/1993 | European Pat. Off. . | |
| 567 105 | 10/1993 | European Pat. Off. . | |
| 2711057 | 4/1995 | France . | |
| 2152450 | 12/1990 | Japan . | |
| 2270247 | 3/1994 | United Kingdom | 604/398 |
| 2280095 | 1/1995 | United Kingdom | 604/398 |

*Primary Examiner*—John G. Weiss
*Assistant Examiner*—K. M. Reichle
*Attorney, Agent, or Firm*—Burns, Doane, Swecker & Mathis LLP

[57] ABSTRACT

A disposable diaper with stretchable longitudinal seals. The diaper includes an absorbent pad between a liquid-tight outer backing sheet and a liquid-pervious inner surface sheet including an elongate opening. Two first longitudinal folds extend over the length of the diaper on either side of the longitudinal opening so that each fold defines a closed sleeve including a stretched resilient member. At least two additional longitudinal folds extend over the length of the diaper and are arranged between the first longitudinal folds and a longitudinal region in which the surface sheet is attached to the diaper.

7 Claims, 1 Drawing Sheet

DISPOSABLE ABSORBENT SANITARY ARTICLE WITH STRETCHABLE LONGITUDINAL SEALS FORMING A POUCH

TECHNICAL FIELD

Background of the Invention

In general terms, the invention relates to a disposable absorbent sanitary article, such as an open disposable absorbent diaper intended for young children or incontinent adults, or a disposable absorbent diaper intended for the toilet-training of children, of the type comprising an absorbent pad placed between a liquid-tight outer backing sheet and a liquid-pervious inner surface or covering sheet.

The invention relates more particularly to a disposable absorbent sanitary article of this type whose inner surface sheet includes an elongate longitudinal opening, for receiving the urine and stools, and at least two elasticated longitudinal folds extending over the whole length of said sanitary article on either side of the longitudinal opening so as to form a leaktight, exudate-containing pouch.

Sanitary articles of this type are known, for example, from U.S. Pat. No. 4,662,877 (Johnson & Johnson). According to that document, the inner surface sheet of the sanitary article is hydrophobic and is provided with an elongate opening which is offset toward the front of the article. The longitudinal edges of the opening are provided with resilient elements which are fixed in the stretched state.

French patent application FR-A-9210601 (Peaudouce) also describes a diaper whose inner surface sheet includes an elongate central opening and two elasticated longitudinal double folds extending over the whole length of the diaper and located on either side of the central opening. The two pleats of each double fold are secured to each other over the whole length of the double folds.

French patent application FR-93 14 296 (Peaudouce), which has not been published, also describes a diaper of the same type, with the double folds being capable of being folded outwards in a longitudinal region extending from the front transverse edge of the opening as far as the front transverse edge of the diaper, so as to form small longitudinal seals to prevent urine leaking out.

European patent application EP-A-357 298 (The Procter and Gamble Company) describes a diaper whose urine-pervious surface sheet includes a passage which permits the communication of fecal matter with the absorbent pad so as to isolate said matter from the user's skin. This passage is an oblong opening which is slightly offset toward the rear of the article. Resilient elements are fixed to the surface sheet close to the opening to cause the surface sheet to contract.

European patent applications EP-A-508 477, EP-A-563 971, EP-A-565 058 and EP-A-567 105 (Uni-Charm Corporation) also describe diapers whose inner surface sheet includes an elongate central opening, this central opening being capable of having one or two pairs of lateral longitudinal flaps whose free edges may be elasticated.

Although these structures described in the prior art are relatively effective, it would still be desirable to improve the take-up and isolation of bodily exudates, such as stools and urine, and also to improve the leak-tightness to prevent risks of transverse leaks of urine. The object of the invention is therefore to provide a disposable absorbent sanitary article which not only provides better take-up and storage of exudates but also improved leaktightness to prevent transverse leaks of urine.

SUMMARY OF THE INVENTION

According to the invention, a disposable absorbent sanitary article, such as a diaper, is produced, said article comprising a liquid-tight outer backing sheet of generally rectangular shape, an absorbent pad of generally rectangular shape fixed on said outer backing sheet, and of a liquid-pervious inner surface sheet covering the absorbent pad. This inner surface sheet is fixed over its periphery to the outer backing sheet. The sanitary article also comprises fastening means to enable it to be closed around a user's waist.

The article also comprises longitudinal resilient elements fixed in the stretched state to the backing sheet outside the longitudinal edges of the absorbent pad, at least in a crotch region.

The liquid-pervious inner surface sheet has a longitudinal opening of generally oblong or elongate shape which is centered on the absorbent pad and narrower than the latter. The inner surface sheet is also directly or indirectly fixed to the absorbent pad, except in a region located below the opening, which is preferably larger than the opening so as to form a continuous containment pouch above the absorbent pad which comprises two longitudinal sealing flaps, extended by two transverse flaps, the free edges of which are formed by the edges of the longitudinal opening.

The inner surface sheet also comprises at least two first longitudinal folds which are substantially parallel to the median longitudinal axis of the article and extend over the whole length of said article on either side of the longitudinal opening, forming closed tubular sleeves in which at least one longitudinal resilient element is fixed, in the stretched state.

According to the invention, the inner surface sheet has at least two additional longitudinal folds extending over the whole length of the article and arranged respectively between each of the first longitudinal folds and the corresponding lateral longitudinal region in which the inner surface sheet is fixed to the rest of the article. According to a preferred embodiment, each of these additional folds is secured to the inner surface sheet at each of its longitudinal ends, close to the transverse edges of the article, in a first, shorter region; each of these folds is free to unfold in a second region correspond to the greater part of the length of the article. Since these additional folds are free to unfold over practically their whole length through the action of the first elasticated folds which lift the surface sheet along the longitudinal edges of the opening, a substantial increase in the height of the longitudinal sealing flaps is thus obtained and, therefore, better adaptation of said longitudinal flaps to the user's body, which gives rise to an improvement in the anti-leak efficiency of the containment pouch whilst preserving the same width of the opening. Without the presence of these additional folds, the only other solution for increasing the height of the longitudinal flaps of such a containment pouch would be reducing the width of the opening, but this would be to the detriment of optimum adaptation of the opening to the user's anatomy and of the most effective take-up of the stools and urine by the absorbent pad. In a recommended embodiment, the second region in which the additional longitudinal folds are free to unfold extends over a length which is at least equal to that of the crotch region of the sanitary article and preferably at least equal to that of the opening in the surface sheet. In another recommended embodiment, the closed sleeves of the first longitudinal folds are folded inward in the direction of the longitudinal axis of the sanitary article and fixed to the part lying under the inner surface sheet, for example over their whole length or intermittently, so as to form Z-shaped folds.

According to another preferred embodiment, the additional longitudinal folds are produced by means of Z- or S-shaped folding.

According to another variant embodiment, the absorbent sanitary article also includes a liquid-pervious intermediate sheet located between the absorbent pad and the inner surface sheet, this intermediate sheet covering the pad at least in the region of the longitudinal opening and being fixed to the absorbent pad. This intermediate sheet, fixed to the pad, also preferably extends over the whole length of the absorbent sanitary article and is wider than the longitudinal opening. The inner surface sheet can then be fixed to the intermediate sheet, except, as above, for a region located under the opening.

BRIEF DESCRIPTION OF THE FIGURES

The remainder of the description, which relates to an illustrative and non-limiting embodiment of the invention, relates to the appended figures which show, respectively.

DETAILED DESCRIPTION OF THE PREFERRED EMBODIMENTS

Figure 1:
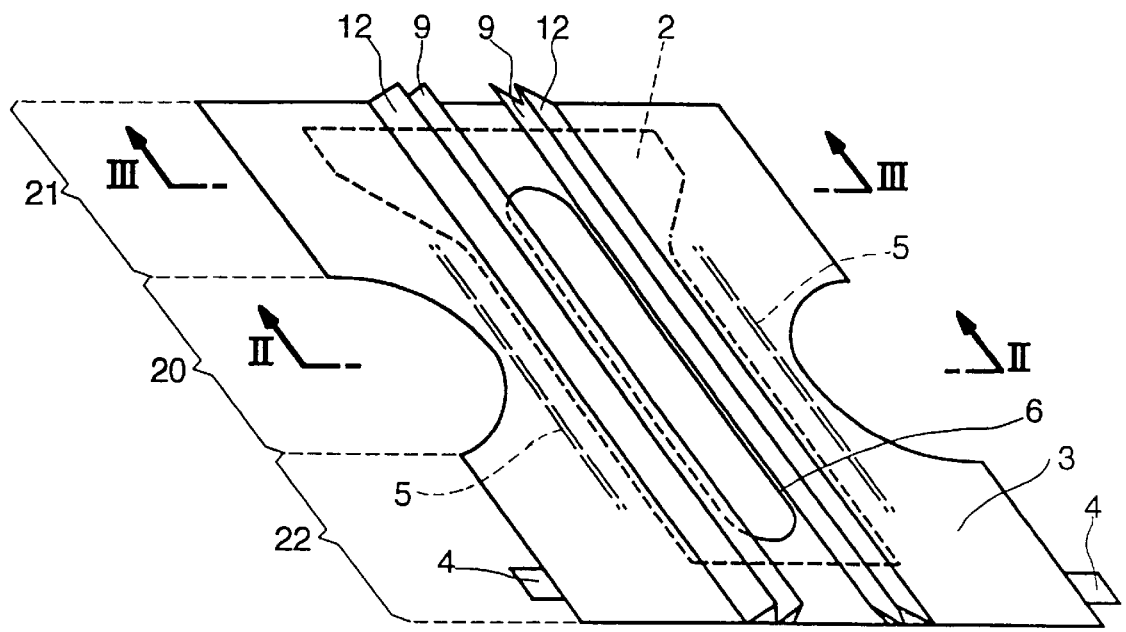
FIG. 1, a perspective top view of a diaper according to the present invention.
Figure 2:
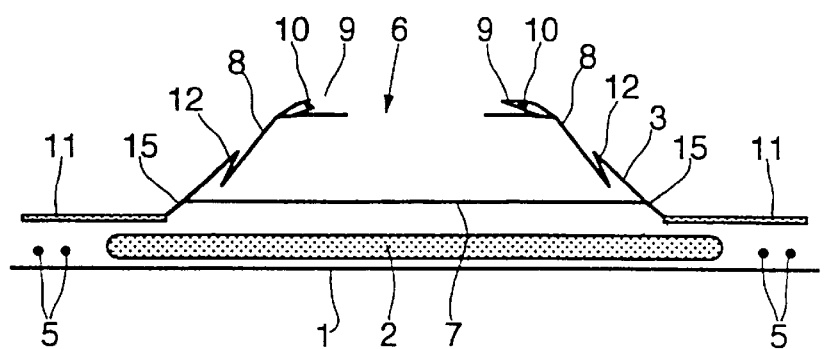
FIG. 2, a diagrammatic sectional view along the line II—II of FIG. 1.
Figure 3:
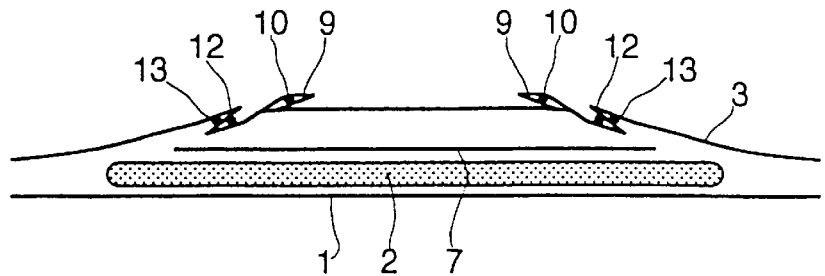
FIG. 3, a diagrammatic sectional view along the line III—III of FIG. 1.

With reference to FIGS. 1 to 3, the diaper shown comprises, in a manner known per se, a liquid-tight backing sheet 1, for example a polyethylene film, an absorbent pad 2, for example made from cellulose fluff pulp with the possible incorporation of particles of superabsorbent material, and a liquid-pervious inner surface sheet 3, for example made from nonwoven web which is hydrophilic or treated so as to have hydrophobic regions. The two sheets 1 and 3 are the same size and have the same hour-glass shape, i.e. a rectangular shape with two opposite lateral notches defining, in the direction of the lengths of the diaper, a narrower crotch region 20 between two wider front 21 and rear 22 end regions whose transverse edges define the front and rear transverse edges of the diaper.

The absorbent pad 2 placed between the sheets 1 and 3 is T-shaped, but any other shape may be envisaged. The two sheets 1 and 3 are joined together, for example by bonding, over the periphery of the pad 2. Fastening means 4 are provided to enable the diaper to be closed around a user's waist.

Longitudinal resilient elements 5 each consisting, for example, of one or more resilient strands or threads are fixed in the stretched state to the backing sheet 1, at least in the crotch region, between the longitudinal edge of the sheet 1 and the corresponding longitudinal edge of the absorbent pad 2.

As FIG. 1 shows, the inner surface sheet 3 includes an opening 6 which is generally oblong or elongate in shape and is symmetrical with respect to the median longitudinal axis of the diaper, centered above the absorbent pad 2 and narrower than the width of the absorbent pad in the crotch region so as to facilitate the penetration of urine and stools into the pad. This opening is preferably narrower than half the width of the pad 2 in the crotch region.

Quite obviously the dimensions of this opening 6 depend on the size of the user for which the diaper is intended. In an embodiment given by way of example, in the case of a so-called "maxi"-size diaper (8–18 kg), the opening 6 is substantially rectangular and has a length of 300 mm and a width of 50 mm.

The diaper preferably includes a liquid-pervious intermediate strip or sheet 7, for example made from hydrophilic nonwoven, extending over the whole length of the diaper and equal in width to or wider than the width of the absorbent pad 2 in the crotch region and thus also wider than the width of the longitudinal opening 6. Moreover, this intermediate sheet 7 could also be shorter than the diaper and shorter even than the absorbent pad provided it is longer than the opening 6 so as to avoid any direct contact between the skin of the user and the absorbent pad. This intermediate sheet is preferably fixed to the absorbent pad 2. The inner surface sheet 3 is fixed, on the one hand, to this intermediate sheet 7 by bonding lines 15, and, on the other hand, to the rest of the diaper by bonding regions 11, except for a region which is located below the longitudinal opening 6 and is larger than it (for example, in the case of the dimensions of the longitudinal opening 6 which were given above, this region may be a rectangular region 360 mm in length and 100 mm in width), so as to form a continuous containment pouch above and at the periphery of the absorbent pad, comprising two longitudinal sealing flaps 8 extending via two transverse flaps, the free edges of which are formed by the edges of the opening 6.

The surface sheet 3 also includes two parallel longitudinal folds 9 extending over the whole length of the diaper and arranged on either side of the longitudinal opening 6 close to the latter's longitudinal edges. The lower edges of the folds 9 are joined by a longitudinal fixing line, for example a bonding line, over the whole length of the folds, so as to form closed sleeves. Longitudinal resilient elements 10 are placed, in the stretched state, inside the folds in the upper part of the closed sleeves formed by these folds 9. These folds may preferably be folded toward the inside of the diaper in the direction of the latter's median longitudinal axis and be fixed to the part lying under the inner surface sheet 3, for example by a continuous or intermittent bonding line, so as to form Z- or S-shaped double folds.

The surface sheet 3 also has two additional longitudinal folds 12 extending over the whole length of the diaper and arranged symmetrically with respect to the opening 6 between the first folds 9 and the longitudinal regions in which the surface sheet 3 is fixed to the intermediate sheet 7 covering the absorbent pad 2 and to the rest of the diaper.

These additional folds 12 may be obtained by means of a process of folding the surface sheet 3, identical to that used to form the first folds 9, or by means of any other process, and may, for example, have the Z-shape as shown in FIGS. 1 to 3. Other types of folding, however, such as, for example, concertina pleating or S-type folding, may be envisaged.

As shown in FIG. 3, each of these additional folds 12 is secured to the surface sheet 3 at its longitudinal ends close to the transverse edges of the diaper, for example by one or more bonding regions 13 or by any other fixing means (heat sealing, ultrasound) of reduced length, for example from 1 to 2 cm, also enabling the two faces of the fold to be sealed together. In this way, the ends of the folds 12 which could form channels via which urine escapes to the outside of the diaper are closed, thereby preventing risks of leaks longitudinally along these folds.

On the other hand, each fold 12 is free to unfold over the greater part of its length, i.e. over a length which is at least equal to that of the crotch region of the diaper and is preferably at least equal to that of the opening 6.

The formation of a multiplicity of additional folds distributed over the width of each sealing flap 8 may also be envisaged.

When the diaper is placed on the user's body, through the action of the longitudinal resilient elements 10 fixed in the first folds 9, which raise the edges of the opening 6 of the surface sheet 3, unfolding of the folds 12 gives rise to an increase in the height of the longitudinal sealing flaps 8 and thus better adaptation of the latter to the user's body without the width of the opening 6 being modified during the manufacturing process. Indeed, as the height of each longitudinal sealing flap 8 forming the greater part of the containment pouch is defined by the distance between the corresponding longitudinal edge of the opening 6 and the longitudinal line 15 for fixing the surface sheet 3 to the intermediate sheet 7, if this line 15 cannot be shifted toward the longitudinal edges of the diaper for reasons of leaktightness the only possibility which remains at the manufacturing-process level is to reduce the width of the opening 6. In point of fact, such a reduction can only be detrimental to satisfactory take-up and efficient storage of stools and urine.

A diaper which allows better leaktightness on the part of the containment pouch thus formed with respect to leaks of urine is thus produced, while still maintaining excellent take-up and retention of urine and stools in the absorbent pad.

I claim:

1. A disposable diaper having a median longitudinal axis and a longitudinal length and defined by longitudinal and transverse edges, said diaper further comprising:

a liquid-tight outer backing sheet of generally rectangular shape, an absorbent pad of generally rectangular shape with a periphery defined by longitudinal edges and transverse edges, said absorbent pad being fixed on said outer backing sheet, a liquid-pervious inner surface sheet covering the absorbent pad, a periphery of the liquid-pervious inner surface sheet being fixed to the outer backing sheet, fastening means to enable the diaper to be closed around a user's waist, longitudinal resilient elements fixed in a stretched state to the backing sheet outside the longitudinal edges of the absorbent pad, at least in a crotch region of the diaper, said inner surface sheet including a longitudinal opening which is centered on the absorbent pad and narrower than the absorbent pad, said inner surface sheet being fixed to the absorbent pad, except in a region which is located below the longitudinal opening, said region being larger than the longitudinal opening so as to form a containment pouch above and at the periphery of the absorbent pad, said inner surface sheet further including at least two first longitudinal folds which are substantially parallel to the longitudinal opening, each of said folds forming a closed sleeve in which at least one longitudinal resilient element is fixed, in a stretched state, and said inner surface sheet further including at least two additional longitudinal folds with longitudinal ends extending over the longitudinal length of the diaper and arranged laterally respectively between each of the first longitudinal folds and a corresponding lateral longitudinal region in which the inner surface sheet is fixed to the diaper;

wherein each of the at least two additional longitudinal folds is secured to the inner surface sheet at each of the longitudinal ends, close to the transverse edges of the diaper, in a first, shorter region, and each of the at least two additional folds being configured so as to be free to unfold in a second region corresponding to a greater part of the longitudinal length of the diaper.

2. The diaper according to claim 1, wherein the second region in which the at least two additional longitudinal folds are free to unfold extends over a length which is at least equal to that of the crotch region of the diaper.

3. The diaper according to claim 1, wherein the closed sleeves of the first longitudinal folds are folded inward in the direction of the longitudinal axis of the diaper and fixed to a part lying under the inner surface sheet so as to form Z-shaped folds.

4. The diaper according to claim 1, wherein the at least two additional longitudinal folds are produced by means of Z- or S-shaped folding.

5. The diaper according to claim 1, further comprising a liquid-pervious intermediate sheet located between the absorbent pad and the inner surface sheet, said intermediate sheet covering the absorbent pad at least in the region of the longitudinal opening and being fixed to the absorbent pad.

6. The diaper according to claim 5, wherein said intermediate sheet extends over the longitudinal length of the diaper and is wider than the longitudinal opening and the inner surface sheet is fixed to said intermediate sheet, except for said region located below the opening which is larger than the longitudinal opening.

7. The diaper according to claim 1, wherein the second region in which the at least two additional longitudinal folds are free to unfold extends over a length which is at least equal to that of the longitudinal opening in the inner surface sheet.

* * * * *